(12) United States Patent
Inaguma et al.

(10) Patent No.: US 10,988,756 B2
(45) Date of Patent: Apr. 27, 2021

(54) MICROCHIP

(71) Applicant: NEC CORPORATION, Tokyo (JP)

(72) Inventors: Asumi Inaguma, Tokyo (JP); Yasuo Iimura, Tokyo (JP); Minoru Asogawa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 146 days.

(21) Appl. No.: 16/077,251

(22) PCT Filed: Feb. 21, 2017

(86) PCT No.: PCT/JP2017/006421
§ 371 (c)(1),
(2) Date: Aug. 10, 2018

(87) PCT Pub. No.: WO2017/146062
PCT Pub. Date: Aug. 31, 2017

(65) Prior Publication Data
US 2019/0062725 A1 Feb. 28, 2019

(30) Foreign Application Priority Data

Feb. 22, 2016 (JP) .............................. JP2016-030641

(51) Int. Cl.
*C12N 15/10* (2006.01)
*C12N 15/09* (2006.01)
(Continued)

(52) U.S. Cl.
CPC .... *C12N 15/1003* (2013.01); *B01L 3/502715* (2013.01); *C12N 15/09* (2013.01);
(Continued)

(58) Field of Classification Search
None
See application file for complete search history.

(56) References Cited

U.S. PATENT DOCUMENTS 5,863,801 A * 1/1999 Southgate ........... B01L 3/50273
422/417
8,431,340 B2 4/2013 Jovanovich et al.
(Continued)

FOREIGN PATENT DOCUMENTS

| JP | 2008-513022 A | 5/2008 |
|---|---|---|
| JP | 2013521780 A | 6/2013 |

(Continued)

OTHER PUBLICATIONS

International Search Report of PCT/JP2017/006421 dated May 23, 2017.
(Continued)

*Primary Examiner* — Samuel C Woolwine
(74) *Attorney, Agent, or Firm* — Sughrue Mion, PLLC

(57) ABSTRACT

A microchip comprises a DNA analysis part configured to analyze DNA, which comprises at least a cell lysis chamber for cell lysis and a DNA extraction chamber which is connected to the cell lysis chamber and configured to extract DNA from lysed cells, and a DNA preservation part which is connected to the DNA analysis part via a flow path and configured to preserve a partial portion of a DNA sample.

8 Claims, 9 Drawing Sheets

(51) Int. Cl.
*B01L 3/00* (2006.01)
*C12Q 1/68* (2018.01)
*C12Q 1/6837* (2018.01)
*B01L 7/00* (2006.01)
*B01L 9/00* (2006.01)

(52) U.S. Cl.
CPC ............ *C12Q 1/68* (2013.01); *C12Q 1/6837* (2013.01); *B01L 3/5029* (2013.01); *B01L 7/52* (2013.01); *B01L 9/527* (2013.01); *B01L 2200/10* (2013.01); *B01L 2300/043* (2013.01); *B01L 2300/0864* (2013.01); *B01L 2300/0887* (2013.01); *B01L 2400/0421* (2013.01); *B01L 2400/0481* (2013.01); *B01L 2400/0487* (2013.01); *B01L 2400/0666* (2013.01)

(56) References Cited

U.S. PATENT DOCUMENTS

| | | | |
|---|---|---|---|
| 8,431,390 B2 | 4/2013 | Jovanovich et al. | |
| 8,551,714 B2 | 10/2013 | Jovanovich et al. | |
| 8,623,294 B2 | 1/2014 | Asogawa et al. | |
| 8,741,231 B2 | 6/2014 | Asogawa et al. | |
| 9,354,199 B2 | 5/2016 | Selden et al. | |
| 2007/0248958 A1 | 10/2007 | Jovanovich et al. | |
| 2010/0068723 A1 | 3/2010 | Jovanovich et al. | |
| 2011/0000561 A1 | 1/2011 | Asogawa et al. | |
| 2011/0220502 A1 | 9/2011 | Selden et al. | |
| 2012/0055798 A1* | 3/2012 | Selden .............. B01L 3/502753 204/600 |
| 2012/0088249 A1 | 4/2012 | Jovanovich et al. | |
| 2013/0029338 A1 | 1/2013 | Jovanovich et al. | |
| 2013/0248366 A1 | 9/2013 | Haswell et al. | |
| 2014/0079605 A1 | 3/2014 | Asogawa et al. | |
| 2014/0134077 A1 | 5/2014 | Yotoriyama et al. | |
| 2017/0106369 A1 | 4/2017 | Asogawa et al. | |

FOREIGN PATENT DOCUMENTS

| | | |
|---|---|---|
| JP | 2013-537043 A | 9/2013 |
| JP | 2014-098595 A | 5/2014 |
| WO | 2009/119698 A1 | 10/2009 |
| WO | 2014/034952 A1 | 3/2014 |
| WO | 2015/141790 A1 | 9/2015 |

OTHER PUBLICATIONS

Communication, dated Dec. 1, 2020, from the Japanese Patent Office in Japanese Patent Application No. 2019-202230.

* cited by examiner

MICROCHIP

DESCRIPTION OF RELATED APPLICATION

This application is a National Stage of International Application No. PCT/JP2017/006421 filed Feb. 21, 2017, and claims the benefit of Japanese Patent Application No. 2016-030641, filed on Feb. 22, 2016, which is hereby incorporated by reference herein in its entirety. This invention relates to a microchip for analyzing a DNA sample.

FIELD

Background

A technology for executing DNA analysis processes, such as DNA extraction, PCR and electrophoresis, on a microchip has been developed (for example, Patent Literature 1). In addition, an injection tool for injecting a sample solution into the microchip (for example, Patent Literature 2) has been also developed.

When the injection tool is used, it is required to execute a pretreatment before injection of the sample solution into the microchip. Therefore, a microchip has been recently developed, in which the pretreatment is also executed automatically. That is, in a case where this microchip is used, a user is only required to load a swab to which subject's cells are attached onto the microchip, while cell lysis, DNA extraction, PCR, and electrophoresis are automatically executed on the microchip.
[Patent Literature 1]
International Application Publication WO2009/119698A
[Patent Literature 2]
Japanese Patent Kokai Publication No. 2014-098595A

SUMMARY

The following analysis was made from an aspect of the present invention. Each disclosure of the Prior art documents is incorporated by reference herein.

Above mentioned microchip is often of a disposable type, thus has a problem that, even if DNA analysis result is required to be re-examined in a laboratory, a sample cannot be subjected to the re-examination, since the sample has been disposed together with the microchip.

Accordingly, it is an object of the present invention to provide a microchip useful for re-examination of a DNA analysis result.

According to a first aspect of the present invention, there is provided a microchip that comprises at least a cell lysis chamber for cell lysis and a DNA extraction chamber which is connected to the cell lysis chamber and configured to extract DNA from lysed cells, and comprises a DNA analysis part configured to analyze DNA, and a DNA preservation part which is connected to the DNA analysis part via a flow path and configured to preserve (keep) a partial portion of a DNA sample.

According to the first aspect of the present invention, there is provided a microchip useful for re-examination of a DNA analysis result.

PREFERRED MODES

Preferable exemplary embodiments of the present invention will be explained in detail below with reference to drawings. Herein, reference symbols in the following description are expediently attached to each element as an example of explanatory aid for understanding, but not intended to limit the present invention to an illustrated configuration(s).

Figure 1:
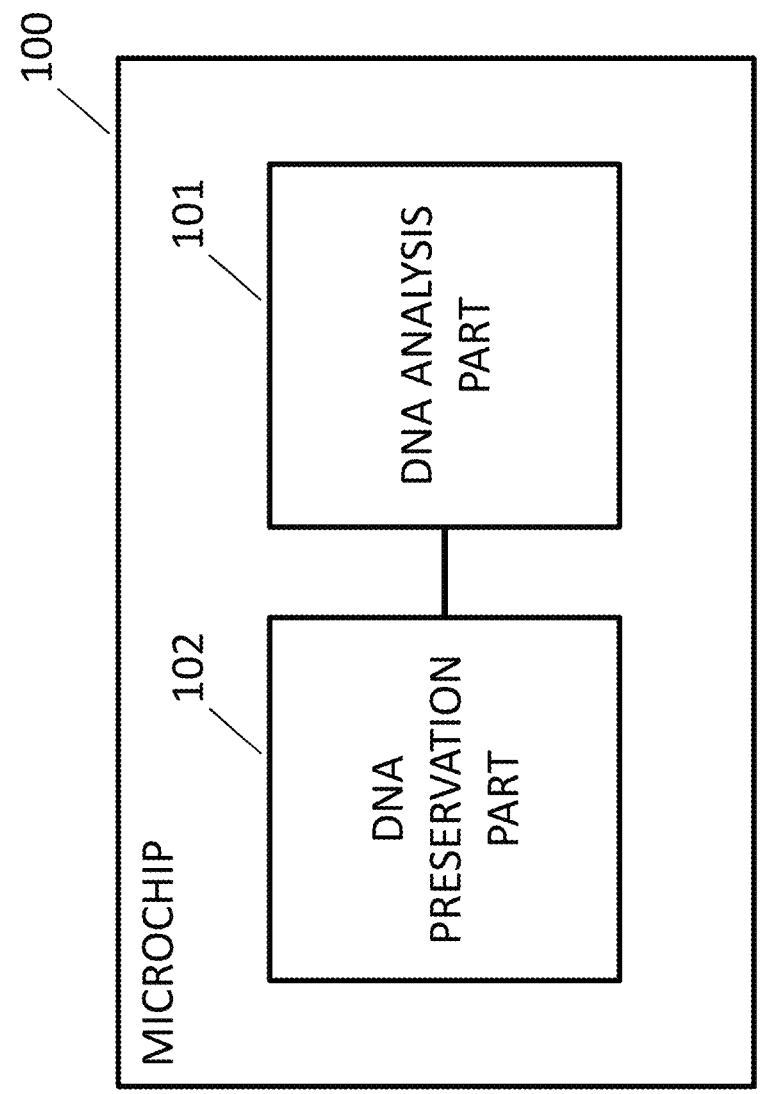
FIG. 1 is an explanatory schematic view of a microchip of one exemplary embodiment.

FIG. 1 is an explanatory schematic view of a microchip of one exemplary embodiment. As illustrated in FIG. 1, a microchip 100 comprises a DNA analysis part 101 and a DNA preservation part 102. The DNA analysis part 101 comprises at least a cell lysis chamber for cell lysis and a DNA extraction chamber which is connected to the cell lysis chamber and configured to extract DNA from lysed cells. The DNA preservation part 102 is connected to the DNA analysis part 101 via a flow path.

On the microchip 100, a partial portion of a DNA sample is utilized for DNA analysis on the DNA analysis part 101, and remaining DNA sample is preserved in the DNA preservation part 102. After use of the microchip 100, an operator recovers the preserved DNA sample from the DNA preservation part 102 and keeps it separately. Thereby, the operator may conduct re-examination of a DNA analysis result by using the preserved DNA sample.

Concrete exemplary embodiments will be explained below in more detail with reference to drawings. Herein, in each exemplary embodiment, the same reference symbol is attached to the same component, and thus explanation for the same component will be omitted.

First Exemplary Embodiment

Figure 2:
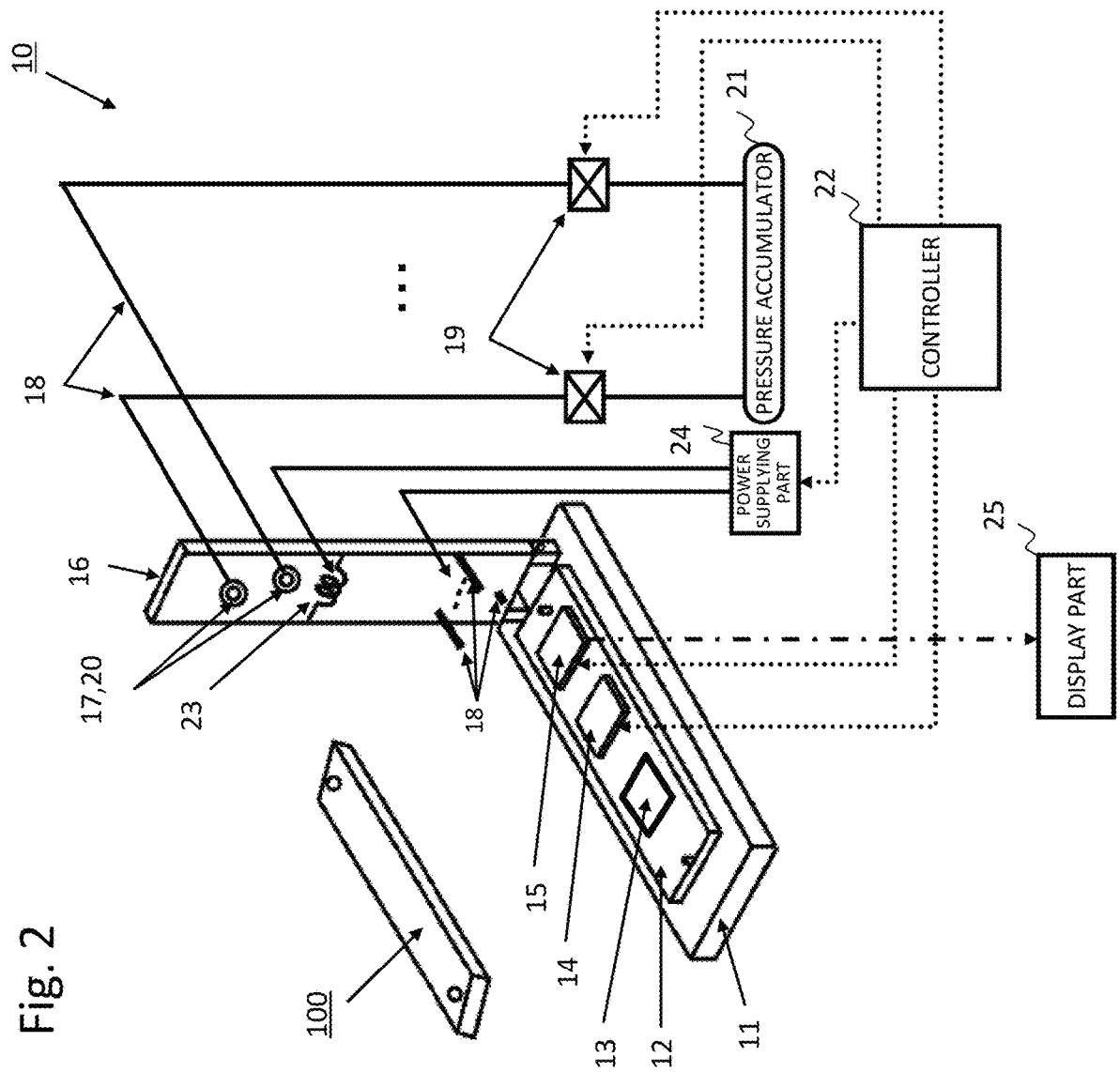
FIG. 2 is an exemplary view concretely illustrating a microchip controlling apparatus 10.

A concrete example of microchip, a microchip controlling apparatus and a microchip controlling system in a first exemplary embodiment will be exemplified with reference to drawings. As illustrated in FIG. 2, a microchip controlling apparatus 10 has a configuration that a table 12 is arranged on a base plate 11, and a cell lysis unit 13, a PCR unit 14, an electrophoresis unit 15 are mounted on the table 12. In addition, the base plate 11 and a lid 16 are jointed with a hinge in a manner where the lid 16 may be opened and closed.

A microchip 100 is placed on a predetermined position on the table 12 in such a manner that pins arranged on the table 12 are inserted into pin holes arranged on the microchip 10. A plurality of pressurizing holes 17 are arranged on the lid 16. On the lid 16, regions corresponding to pressurizing holes 17 are formed as through holes, and the pressurizing holes 17 are connected to solenoid valves 19 via tubes 18.

In addition, when the lid 16 is closed, the pressurizing holes 17 are connected to a variety of control holes on the microchip 100. Herein, it is preferable that the pressurizing holes 17 are made into contact with the control holes with interposed sealing mechanisms, such as O-rings 20.

A pressure accumulator 21 stores pressurizing medium, such as compressed air. A controller 22 controls the solenoid valves 19 so as to charge/discharge the pressurizing medium into/from the control holes on the microchip 100 via the pressurizing holes 17. Herein, internal pressure in the pressure accumulator 21 is controlled by a pressure sensor and a pump (not shown) so as to be maintained at a predetermined pressure.

A DNA extracting unit 23 is mounted on the lid 16, which is configured to extract DNA from lysed cells. The DNA extracting unit 23 is exemplified by an electromagnet, a neodymium magnet or the like. Under control by the controller 22, the DNA extracting unit 23 moves the magnet to approach the DNA extraction chamber 121 or moves the magnet away from the DNA extraction chamber 121.

The cell lysis unit 13 and the PCR unit 14 comprise a temperature sensor (s), a heat conductor (s), a Peltier element(s) (thermoelectric element), a heat releasing plate etc. The cell lysis unit 13 performs lysis by heating a solution containing cells, and the PCR unit 14 performs PCR.

The electrophoresis unit 15 is a mechanism for executing capillary electrophoresis and detection of fluorescent labels, which comprises excitation apparatus, such as a halogen lamp, a mercury lamp and laser beams, as well as s filter(s) and a camera(s). When DC voltage is applied to an electrode via a power supplying part 24 to start the capillary electrophoresis, the electrophoresis unit 15 monitors fluorescent labels flowing through capillaries and outputs a detection result showing fluctuations in fluorescence intensity over a time course via a display part 25.

Herein, the controller 22 may be realized by a computer installed in the microchip controlling apparatus 10 with a computer program 165 which makes its hardware to execute processes by the microchip controlling apparatus 10 described below.

Figure 3A:
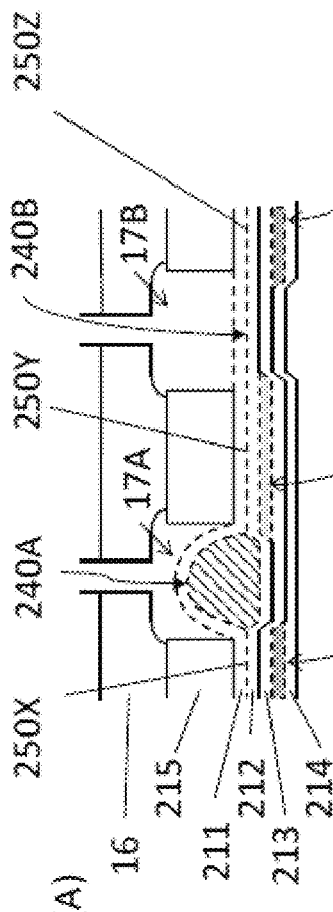
FIGS. 3(A)-3(C) are explanatory views of an example of a flow path control mechanism on the microchip 100.
Figure 3B:
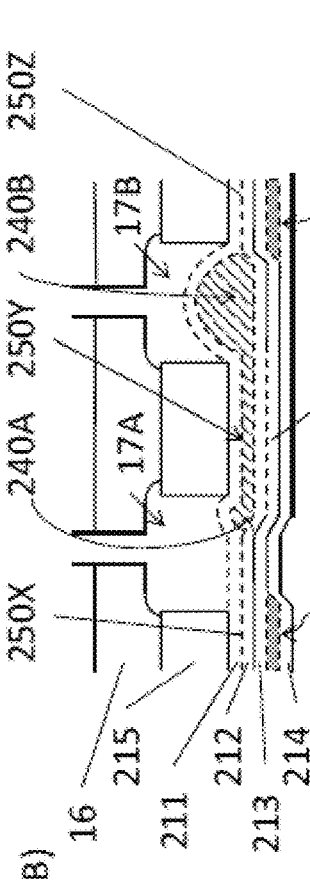
Figure 3C:
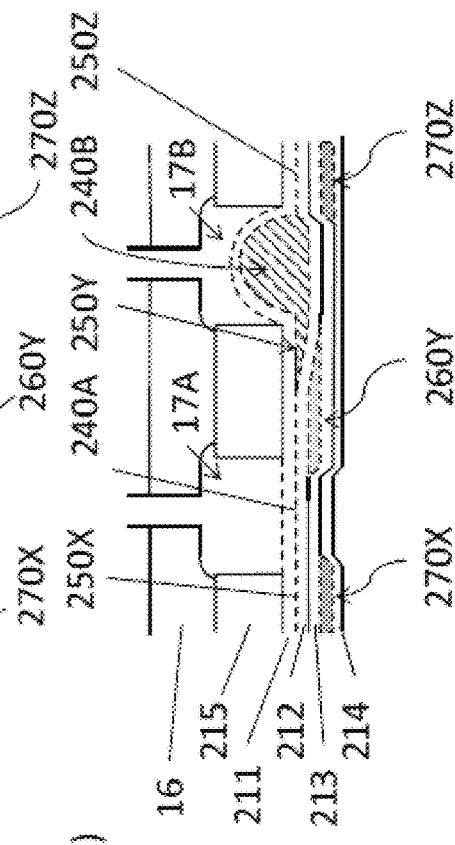

A microchip 100 has a laminated configuration of elastic sheets 211 to 214 and a resin plate 215 as illustrated in FIGS. 3(A)-3(C). The elastic sheets 211 to 214 preferably are made of a material having a heat resistance, acid/alkali resistance, and elastic property, such as silicone rubber etc. as main material, and the resin plate 215 preferably has a hardness in an extent capable of regulating extension of the elastic sheets 211 to 214. The elastic sheets 211 to 214 are formed (adhered) with partial inadhesive sections, and the inadhesive sections form liquid chambers, flow paths, valve mechanisms and the like. Herein, broken lines in FIGS. 3(A)-3(C) indicate inadhesive sections. In addition, the valve mechanism is also referred to as a flow path opening/closing mechanism.

Here, with reference to FIGS. 3 (A) to (C), an example of flow path control mechanism on the microchip 100 will be explained. As illustrated in FIGS. 3 (A) to (C), a liquid chamber 240A is formed between an elastic sheet 211 and an elastic sheet 212 on the microchip 100 and connected to flow paths 250X and 250Y. A site corresponding to the liquid chamber 240A on a resin plate 215 is a through control hole, and pressurizing medium may be charged into/discharged from an upper section above the liquid chamber 240A through a pressurizing hole 17A arranged on the lid 16. Similarly, a liquid chamber 240B is connected to flow paths 250Y and 250Z, and pressurizing medium may be charged into/discharged from an upper section above the liquid chamber 240B through a pressurizing hole 17B. The flow path 250X, 250Y are in a closed state.

Under such premise, the microchip controlling apparatus 10, as illustrated in FIG. 3(A), initially injects the pressurizing medium into a valve mechanism 270Z so as to close the flow path 250Z, and then releases the pressurizing medium from a valve mechanism 260Y so as to open the flow path 250Y. After that, the microchip controlling apparatus 10 applies the pressurizing medium to the liquid chamber 240A through the pressurizing hole 17A. As a result, as illustrated in FIG. 3(B), liquid squeezed out from the liquid chamber 240A reaches the liquid chamber 240B through the flow path 250Y and pushes up the elastic sheet 211 to be accumulated in the liquid chamber 240B. Then, when it is determined that impressed pressure onto the liquid chamber 240A with the pressurizing medium exceeds a predetermined value and that the liquid is discharged from the liquid chamber 240A, the microchip controlling apparatus 10 injects the pressurizing medium into the valve mechanism 260Y from upstream side of the flow path 250Y (i.e., the side of the liquid chamber 240A) as illustrated in FIG. 3(C). As a result, liquid in the flow path 250Y is squeezed out into the liquid chamber 240B, whereupon liquid transfer is completed. After that, since it is not required to close the flow path 250X, the microchip controlling apparatus 10 releases the pressurizing medium from the valve mechanism 270X.

Figure 4A:
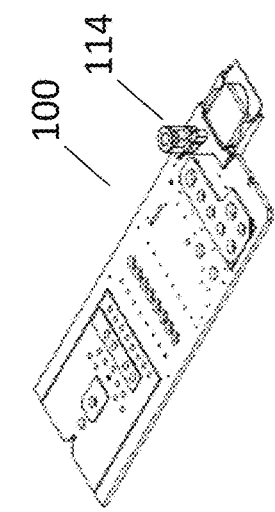
FIGS. 4(A)-4(C) are exemplary views concretely illustrating the microchip 100.
Figure 4B:
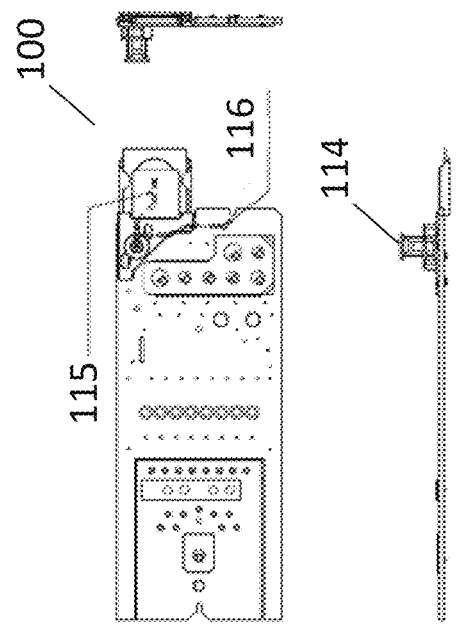
Figure 4C:
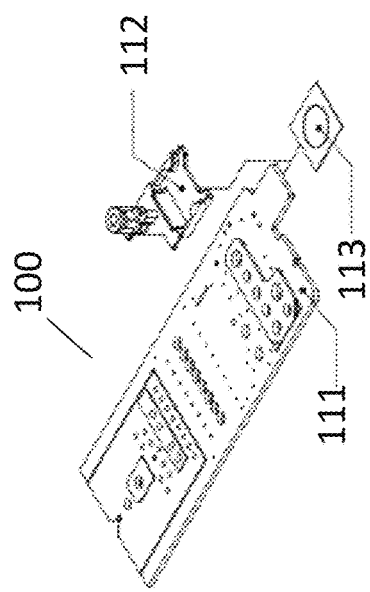

FIGS. 4(A)-4(C) are exemplary views concretely showing the microchip 100. FIG. 4(A) is a perspective view of the microchip 100, FIG. 4(B) is three-sight views of the microchip 100, and FIG. 4(C) is an exploded view of the microchip 100. As illustrated in FIGS. 4(A)-4(C), the microchip 100 comprises a chip main body 111, a card case 112 attached to the chip main body 111, and a DNA absorption card 113 inserted into the card case 112. A swab acception part 114 is integrally arranged on the card case 112. The swab acception part 114 and the DNA absorption card 113 are communicated via a flow path 115, and the flow path 115 is opened and closed by a valve mechanism 116. Herein, the DNA analysis part 101 illustrated in FIG. 1 corresponds to the chip main body 111 and the swab acception part 114, and the DNA preservation part 102 corresponds to the card case 112 and the DNA absorption card 113. In addition, DNA absorption card 113 is also referred to as a solution absorptive medium, comprising a cellulose sheet, for example, FTA (registered trade mark) card. Herein, the card case 112 and the DNA absorption card 113 may be integrally formed with the chip main body 111, and preferably DNA absorption card 113 is configured to be easily separatable from the chip main body 111 by an operator after use thereof.

Figure 5:
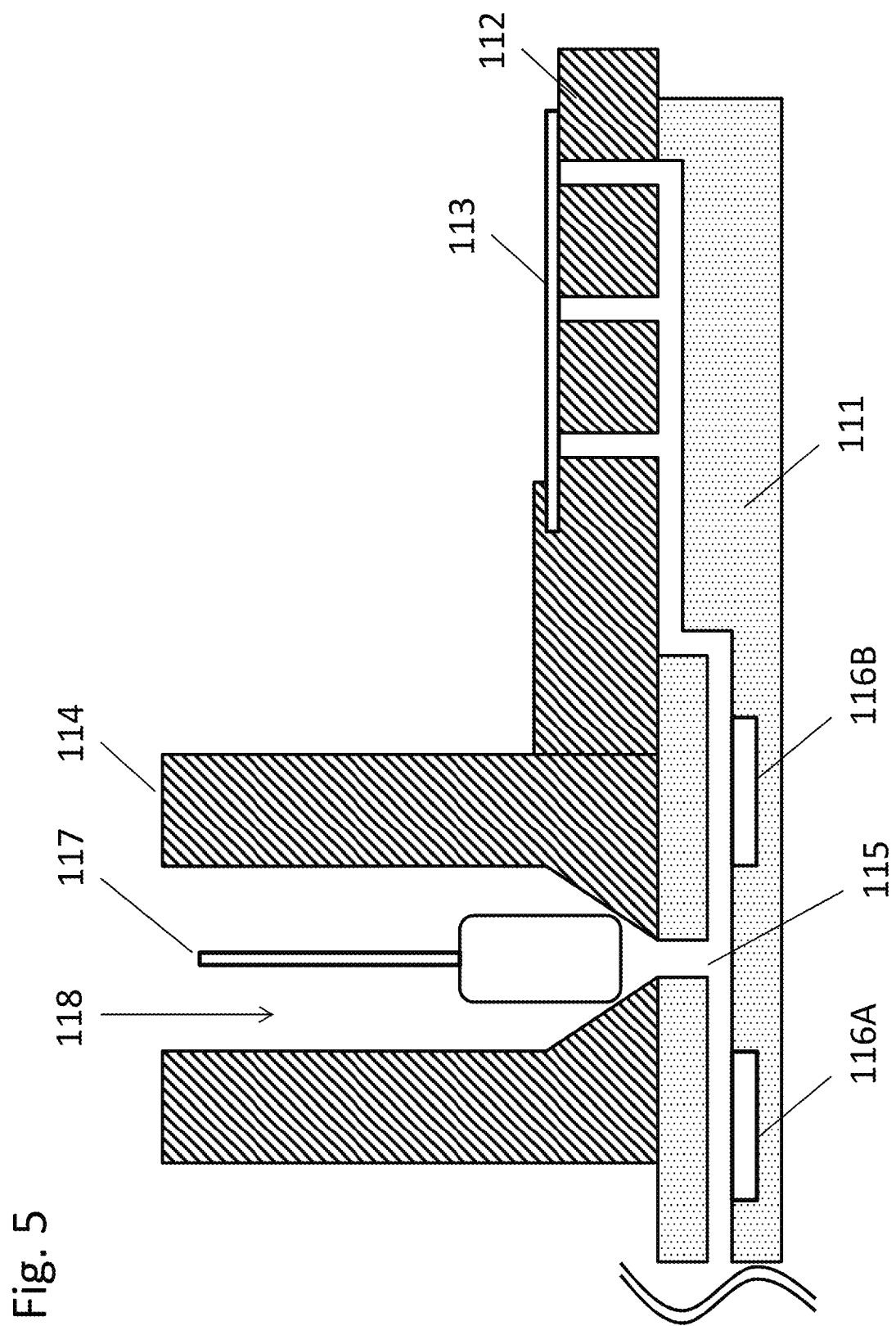
FIG. 5 is an exemplary view concretely illustrating the microchip 100.

As illustrated in FIG. 5, the swab acception part 114 has a cylindrical shape, into which a swab (cotton swab) 117 to which cells are attached is inserted from an upper opening part. Inner space of the swab acception part 114 corresponds to a cell lysis chamber 118, into which cell lysis buffer flows from a side of the chip main body 111 through a lower opening part. A flow path 115 is configured with an inadhesive section between elastic sheets in the chip main body 111, a groove arranged on a surface of the chip main body 111 and through holes formed on the card case 112. In addition, the flow path 115 comprises a branch part branching off into multiple branches, and opening end parts of the branch part respectively contact with different regions on the DNA absorption card 113. That is, the opening end parts are arranged so that cell lysis solution is absorbed in the entire of the DNA absorption card 113, being arranged at a top of a triangle, for example. Flow path control similar to that illustrated in FIGS. 3(A)-3(C) is also executed on the cell lysis chamber 118 in FIG. 5. That is, in a case where cell lysis solution is transferred to a side of the DNA analysis part, under a condition where a valve mechanism 116A is opened and a valve mechanism 116B is closed, pressurizing medium flows into the cell lysis chamber 118 so as to push out the cell lysis solution in the cell lysis chamber 118 into the flow path 115. In addition, in a case where the cell lysis solution is transferred to a side of the DNA preservation part 102, under a condition where the valve mechanism 116A is closed and the valve mechanism 116B is opened, the pressurizing medium flows into the cell lysis chamber 118 so as to push out the cell lysis solution in the cell lysis chamber 118 into the flow path 115. Herein, the groove(s) constituting the flow path 115 may be arranged on the card case 112, or an inadhesive section(s) between the elastic sheets and the through holes arranged on the card case 112 may be directly communicated without arranging any grooves.

Figure 6:
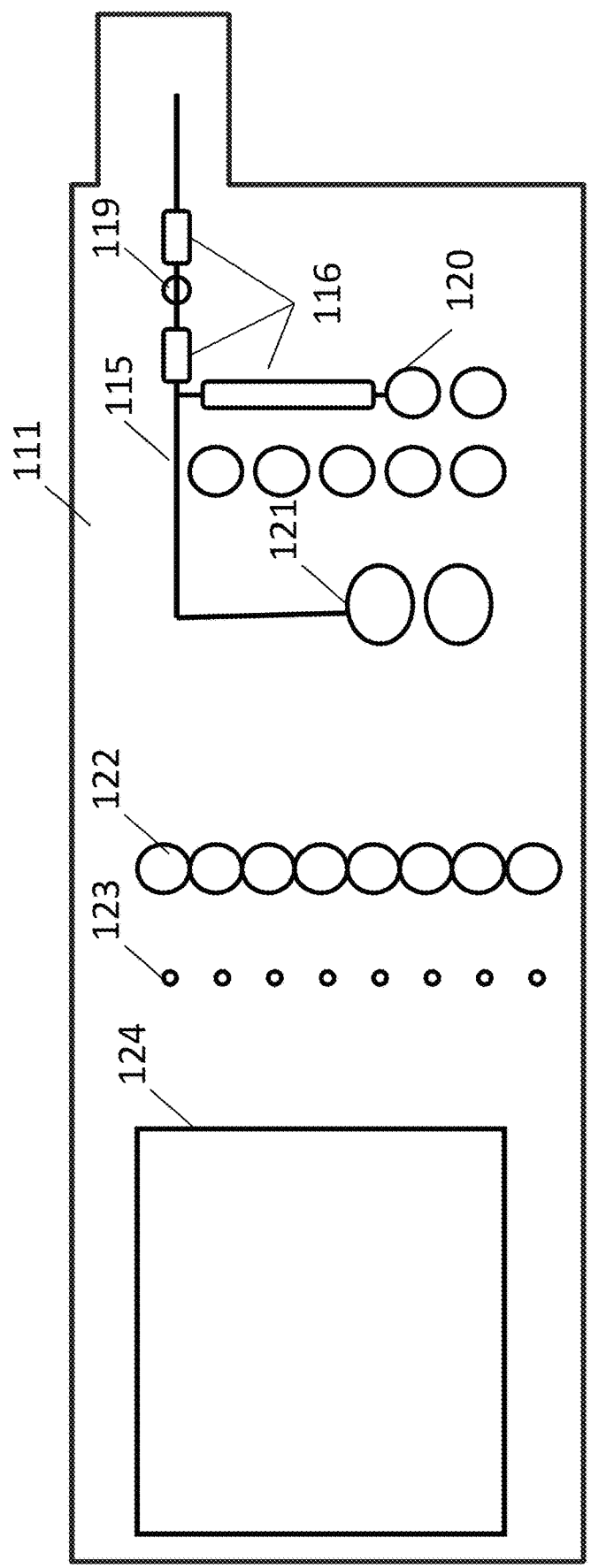
FIG. 6 is an exemplary view concretely illustrating the microchip 100.

FIG. 6 is a view showing an arrangement of solution chambers etc. on the chip main body 111 of FIGS. 4(A)-4(C). Herein, in FIG. 6, the flow path 115 etc. are omitted, except for certain portion(s) thereof. As shown in FIG. 6, the chip main body 111 has an opening part 119 connected to the cell lysis chamber 118. Also, there are arranged on the chip main body 111, buffer/reagent chambers 120, the DNA extraction chamber 121, PCR chambers 122, volume determination chambers 123, and an electrophoresis part 124.

Cell lysis buffer, wash buffer, DNA elution buffer etc. are injected into the buffer/reagent chambers 120. The cell lysis buffer is for example, alkali lysis buffer, and is transferred to the cell lysis chamber 118 through the opening part 119. In a case where heating treatment and the like are required upon lysing cells, mechanisms required for the treatment, for example a heater and a heat conducting plate, are arranged on the microchip controlling apparatus 10 and the swab acception part 114.

The cell lysis solution in the cell lysis chamber 118 is transferred to the DNA extraction chamber 121 and the DNA absorption card 113. Concretely, the microchip controlling apparatus 10 firstly performs a flow path control where the valve mechanism 116A is made into an opened state and the valve mechanism 116B is made into a closed state so that the cell lysis solution in the cell lysis chamber 118 is allowed to be transferred to the DNA extraction chamber 121 (see FIG. 5). Then, the microchip controlling apparatus 10 applies pressurizing medium to the cell lysis chamber 118 so as to transfer the cell lysis solution to the DNA extraction chamber 121. At that time, a partial portion of the cell lysis solution remains in the cell lysis chamber 118, since the volume of the DNA extraction chamber 121 is smaller than that of the cell lysis chamber 118. Subsequently, the microchip controlling apparatus 10 performs a flow path control where the valve mechanism 116A is made into a closed state and the valve mechanism 116B is made into an opened state so that the cell lysis solution in the cell lysis chamber 118 is allowed to be transferred to the DNA absorption card 113 (see FIG. 5). Then the microchip controlling apparatus 10 applies the pressurizing medium to the cell lysis chamber 118 so that the remaining cell lysis solution is absorbed in the DNA absorption card 113.

In (or at) the DNA extraction chamber 121, a DNA extraction process is executed. The DNA extraction process is concretely explained as follows. Magnetic beads (silica) are previously stored in the DNA extraction chamber 121. Subsequent to attachment of DNA contained in the cell lysis solution onto the magnetic beads, the microchip controlling apparatus 10 washes the magnetic beads with a wash buffer(s). Then the microchip controlling apparatus 10 transfers DNA elution buffer from the buffer/reagent chambers 120 to the DNA extraction chamber 121 so that DNA is eluted from the magnetic beads, and further transfers the DNA elution buffer to the PCR chambers 122. Herein, the microchip controlling apparatus 10 makes the magnetic beads to be picked (absorbed) up by a neodymium magnet during discharge of cell lysis solution and the like from the DNA extraction chamber 121 so as to prevent the magnetic beads from being discharged together with the cell lysis solution and the wash buffer.

The DNA extraction method may be changed by making reference to ordinary protocols, for example, increasing the number of washing process. In addition, the DNA extraction method is not limited to a method using the magnetic beads, and for example, a method using a column may be adopted.

At the PCR chambers 122, PCR is executed under temperature control by the PCR unit 14. Concretely, a flow path from the DNA extraction chamber 121 to the PCR chambers 122 is branched, and thereby the DNA elution buffer is separated to flow into each of the PCR chambers 122. Primer set(s) has been stored in the PCR chambers 122 and the DNA elution buffer includes reagents required for PCR reaction, such as a polymerase. Accordingly, the microchip controlling apparatus may execute PCR by making temperature control of the PCR chambers 122 via the PCR unit 14. The temperature control is a temperature control for a hot start process and cycle reaction (a denaturing reaction, an annealing reaction and a primer extension reaction).

The volume determination chambers 123 are mechanisms for determination of the volume of PCR solution containing amplicon, subsequent to the PCR reaction. Concretely, the volume of the volume determination chambers 123 is smaller than that of the PCR chambers and thus liquid transfer is completed under a state where PCR solution in the PCR chambers 122 has not been completely transferred to the volume determination chamber 123. In other words, the microchip controlling apparatus 10 executes the volume determination of PCR solution containing amplicon in such a manner that a partial portion of the PCR solution remains in the PCR chambers 122.

Figure 7:
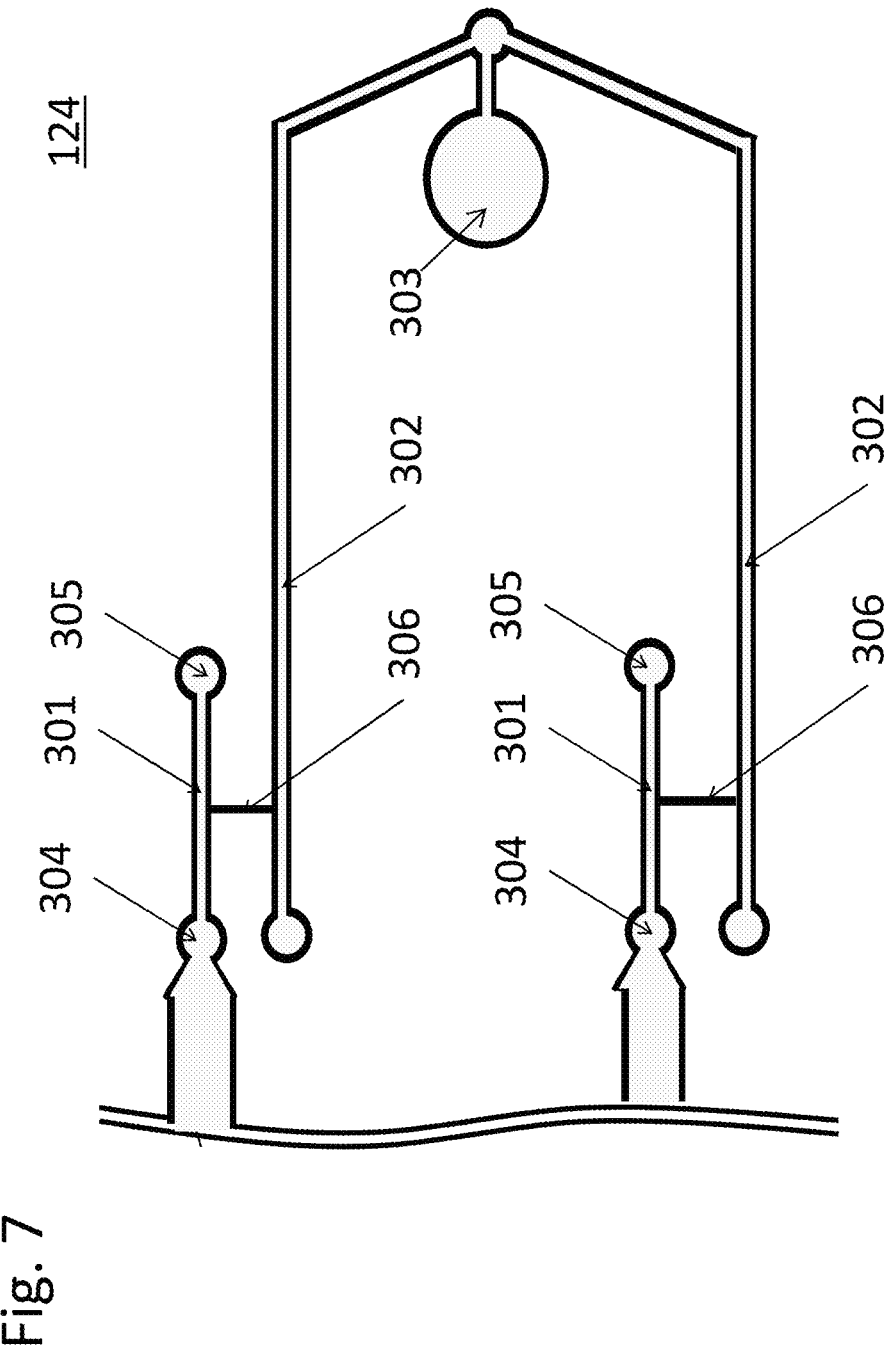
FIG. 7 is an exemplary view concretely illustrating an electrophoresis part 124.

The electrophoresis part 124 comprises sample flow paths 301, capillaries 302 and a polymer chamber 303, as illustrated in FIG. 7. Concretely, the sample flow path 301 is communicated with a volume determination chamber 123 via an electrode chamber 304 and communicated with a reservoir 305 on the opposite end thereof. The reservoir 305 is a mechanism for preventing overflow of a sample flowed into the sample flow path 301. The capillaries 302 are communicated with the polymer chamber 303 via the electrode chamber respectively. In addition, the sample flow path 301 and the capillary 302 extend in parallel and are connected each other via a bridge 306 orthogonal to the sample flow path 301 and the capillary 302. An electrode mounted on the lid 16 is inserted into the electrode chamber 304.

The microchip controlling apparatus 10 fills the capillaries 302 and the bridges 306 with polymer and performs sample injection, and then executes electrophoresis. During electrophoresis, the microchip controlling apparatus 10 monitors label(s) flowing through the capillaries with an electrophoresis unit 15 and outputs a detection result showing fluctuations in fluorescence intensity over a time course via a display part 25.

Figure 8:
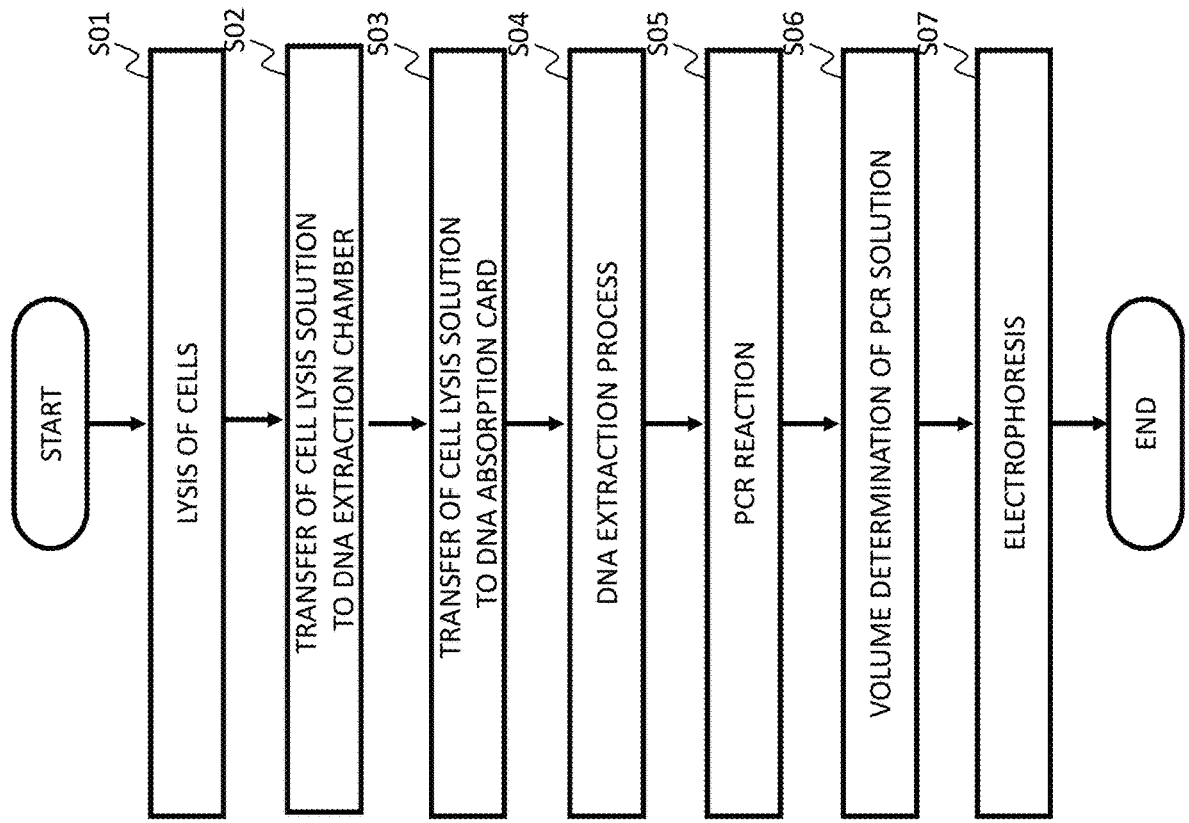
FIG. 8 is a flowchart of processes executed by a microchip controlling apparatus 10.

Hereinafter, flow sequence of processes executed by the microchip controlling apparatus 10 will be briefly explained. FIG. 8 is a flowchart of processes executed by the microchip controlling apparatus 10. As illustrated in FIG. 8, the microchip controlling apparatus 10 transfers the cell lysis buffer to the cell lysis chamber 118 so as to perform lysis of cells (Step S01). Then the microchip controlling apparatus 10 transfers a partial portion of the cell lysis solution to DNA extraction chamber 121 (Step S02) and allows remaining cell lysis solution to be absorbed in the DNA absorption card 113 (Step S03). Then the microchip controlling apparatus 10 executes DNA extraction process (Step S04) and executes PCR reaction (Step S05). Then the microchip controlling apparatus 10 executes volume determination of the PCR solution (Step S06), and executes electrophoresis (Step S07).

Accordingly, in the microchip 100 of the first exemplary embodiment, a partial portion of a DNA sample is utilized for DNA analysis on the DNA analysis part 101 and the remaining DNA sample is preserved in the DNA preservation part 102. After use of the microchip 100, an operator recovers the preserved DNA sample from the DNA preservation part 102 and keeps it separately. Thereby, the operator may conduct re-examination of a DNA analysis result by using the preserved DNA sample.

Second Exemplary Embodiment

The first exemplary embodiment explains a case where the cell lysis chamber 118 and the DNA absorption card 113 are communicated and the DNA absorption card 113 absorbs the cell lysis solution containing DNA, i.e. a case where DNA sample is a cell lysis solution. Similarly, second exemplary embodiment explains a case where the DNA absorption card 113 absorbs a DNA elution buffer containing DNA, i.e. a case where the DNA sample is a DNA elution buffer.

Figure 9:
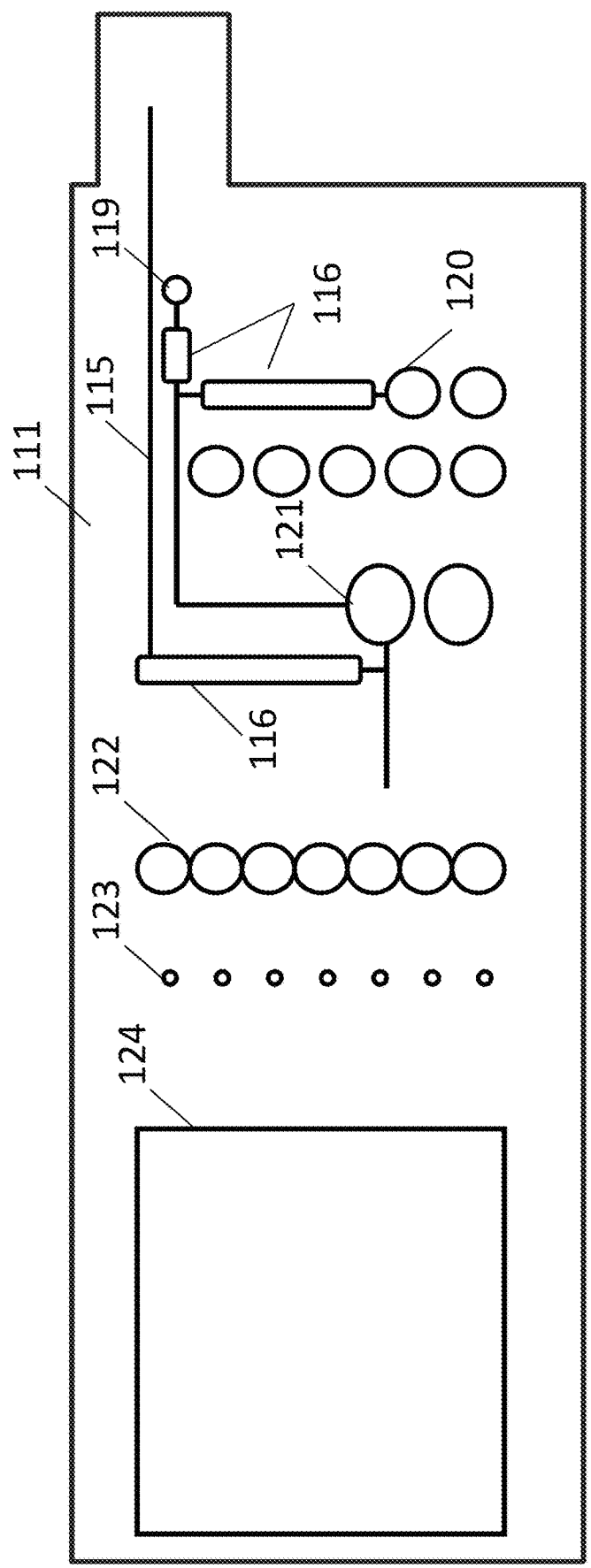
FIG. 9 is an exemplary view concretely illustrating the microchip 100 according to a second exemplary embodiment.

In a concrete example, as illustrated in FIG. 9, on the microchip 100 of second exemplary embodiment, an opening part 119 connected to the cell lysis chamber 118 is connected to buffer/reagent chambers 120 and a DNA extraction chamber 121. In addition, the DNA extraction chamber 121 is connected with DNA absorption card 113 via a downstream flow path 115.

In the second exemplary embodiment, the microchip controlling apparatus 10 transfers the DNA elution buffer from the DNA extraction chamber 121 to PCR chambers 122, subsequent to a DNA extraction process. The volume of the PCR chamber 122 is smaller than that of the DNA extraction chamber 121, thus a partial portion of the DNA elution buffer remains in the DNA extraction chamber 121. Then the microchip controlling apparatus 10 performs flow path control so that the DNA elution buffer in the DNA extraction chamber 121 is allowed to be transferred to the DNA absorption card 113, and then the remaining cell lysis solution is absorbed into the DNA absorption card 113.

Accordingly, in the microchip 100 of the second exemplary embodiment, the DNA sample subsequent to the extraction process may be preserved. Herein, although the PCR solution may also be preserved in a similar manner, it is preferable to preserve the DNA sample subsequent to the lysis process or extraction process if the point of re-examination of a DNA analysis result is taken into account.

A part or the entire of the above mentioned exemplary embodiments may be described as the following modes, but not limited to them.
(MODE 1)
A microchip, wherein the microchip comprises:
a DNA analysis part configured to analyze DNA, which comprises at least a cell lysis chamber for cell lysis and a DNA extraction chamber which is connected to the cell lysis chamber and configured to extract DNA from lysed cells, and
a DNA preservation part which is connected to the DNA analysis part via a flow path and configured to preserve a partial portion of a DNA sample.
(MODE 2)
The microchip of MODE 1, wherein the DNA preservation part is connected to the cell lysis chamber via the flow path.
(MODE 3)
The microchip of MODE 1, wherein the DNA preservation part is connected to the DNA extraction chamber via the flow path.
(MODE 4)
The microchip of any one of MODES 1 to 3, wherein the DNA preservation part comprises a solution absorptive medium, and the solution absorptive medium absorbs the DNA sample.
(MODE 5)
The microchip of MODE 4, wherein the solution absorptive medium is detachably arranged on the DNA preservation part.
(MODE 6)
The microchip of MODE 5, wherein the solution absorptive medium comprises a cellulose sheet.
(MODE 7)
The microchip of MODE 6, wherein the flow path comprises a branch part which branches off into multiple branches, and opening end parts of the branch part respectively contact with different regions on the solution absorptive medium.
(MODE 8)
The microchip of any one of MODES 1 to 7, wherein a swab to which cells are attached is put into the cell lysis chamber.
(MODE 9)
The microchip of any one of MODES 1 to 8, wherein the microchip comprises a flow path opening/closing mechanism configured to open and close the flow path.
(MODE 10)
A DNA analysis method, wherein the method includes:
preparing a microchip which comprises at least a cell lysis chamber for cell lysis, a DNA extraction chamber which is connected to the cell lysis chamber and configured to extract DNA from lysed cells, and a DNA preservation part which is connected to the DNA analysis part via a flow path and configured to preserve a part of DNA sample,
analyzing DNA on the microchip, and
preserving a partial portion of a DNA sample on the microchip.
(MODE 11)
A DNA analysis system, wherein the DNA analysis system comprises a microchip and a microchip controlling apparatus configured to control the microchip, in which the microchip comprises:
a DNA analysis part configured to analyze DNA, which comprises at least a cell lysis chamber for cell lysis and a DNA extraction chamber which is connected to the cell lysis chamber and configured to extract DNA from lysed cells, and
a DNA preservation part which is connected to the DNA analysis part via a flow path and configured to preserve a partial portion of DNA sample.

The disclosure of the above identified Patent Literature(s) is incorporated herein by reference thereto. Modification and adjustment of the exemplary embodiments and examples may be made within an ambit of entire disclosure of the present invention (including claims and based on its basic technological idea. In addition, various combinations and selections of various disclosed components (including each element of each claims, each element described in each exemplary embodiment and Examples and each element shown in each figure) may be made within the ambit of Claims of the present invention. That is, the present invention includes a variety of modifications and corrections which may be made by a person skilled in the art according to the entire disclosure including the claims and the technical idea or concept.

The invention claimed is:

1. A microchip, comprising:
   a DNA analysis part configured to analyze DNA, which comprises at least a cell lysis chamber for cell lysis and a DNA extraction chamber which is connected to the cell lysis chamber and configured to extract DNA from lysed cells,
   a DNA preservation part which comprises a solution absorptive medium which absorbs a partial portion of a DNA sample, and
   a flow path communicating the DNA analysis part with the DNA preservation part, wherein the flow path comprises a branch part which branches off into multiple branches, and opening end parts of the branch part respectively contact with different regions on the solution absorptive medium.

2. The microchip of claim 1, wherein the DNA preservation part is connected to the cell lysis chamber via the flow path.

3. The microchip of claim 1, wherein the DNA preservation part is connected to the DNA extraction chamber via the flow path.

4. The microchip of claim 1, wherein the solution absorptive medium is detachably arranged on the DNA preservation part.

5. The microchip of claim 4, wherein the solution absorptive medium comprises a cellulose sheet.

6. The microchip of claim 1, wherein the microchip comprises a flow path opening/closing mechanism configured to open and close the flow path.

7. A DNA analysis method, wherein the method includes:
   preparing a microchip which comprises at least a cell lysis chamber for cell lysis, a DNA extraction chamber which is connected to the cell lysis chamber and configured to extract DNA from lysed cells, a DNA preservation part which comprises a solution absorptive medium which absorbs a partial portion of a DNA sample, and a flow path communicating the DNA analysis part with the DNA preservation part, wherein the flow path comprises a branch part which branches off into multiple branches, and opening end parts of the branch part respectively contact with different regions on the solution absorptive medium,
   analyzing DNA on the microchip, and
   preserving a partial portion of a DNA sample on the microchip.

8. A DNA analysis system, wherein the DNA analysis system comprises a microchip and a microchip controlling apparatus configured to control the microchip, in which the microchip comprises:
   a DNA analysis part configured to analyze DNA, which comprises at least a cell lysis chamber for cell lysis and a DNA extraction chamber which is connected to the cell lysis chamber and configured to extract DNA from lysed cells,
   a DNA preservation part which comprises a solution absorptive medium which absorbs a partial portion of a DNA sample, and
   a flow path communicating the DNA analysis part with the DNA preservation part, wherein the flow path comprises a branch part which branches off into multiple branches, and opening end parts of the branch part respectively contact with different regions on the solution absorptive medium.

* * * * *